United States Patent [19]

Lambert et al.

[11] Patent Number: 5,102,401
[45] Date of Patent: Apr. 7, 1992

[54] EXPANDABLE CATHETER HAVING HYDROPHOBIC SURFACE

[75] Inventors: James M. Lambert, Centerville; Donald D. Solomon, Spring Valley; Delmer R. Rhodes, Centerville, all of Ohio

[73] Assignee: Becton, Dickinson and Company, Franklin Lakes, N.J.

[21] Appl. No.: 570,756

[22] Filed: Aug. 22, 1990

[51] Int. Cl.⁵ .................................... A61M 5/00
[52] U.S. Cl. ....................................... 604/264
[58] Field of Search ............... 604/264, 265, 280, 282

[56] References Cited

U.S. PATENT DOCUMENTS

| | | | |
|---|---|---|---|
| 2,857,915 | 4/1956 | Sheridan | 604/280 |
| 3,645,955 | 2/1972 | Flynn | 604/280 |
| 4,424,305 | 1/1984 | Gould et al. | 525/127 |
| 4,454,309 | 6/1984 | Gould et al. | |
| 4,668,221 | 5/1987 | Luther | |
| 4,678,660 | 7/1987 | McGary et al. | |
| 4,781,703 | 11/1988 | Walker et al. | |
| 4,798,597 | 1/1989 | Vaillancourt | 604/265 |
| 4,798,876 | 1/1989 | Gould et al. | 525/457 |
| 4,810,582 | 3/1989 | Gould et al. | 428/423.1 |
| 4,838,881 | 6/1989 | Bennett | |
| 4,840,622 | 6/1989 | Hardy | |
| 4,846,812 | 7/1989 | Walker et al. | |
| 4,865,870 | 9/1989 | Hu et al. | |
| 4,883,699 | 11/1989 | Aniuk | |
| 4,994,047 | 2/1991 | Walker et al. | 604/265 |

Primary Examiner—C. Fred Rosenbaum
Assistant Examiner—Sharon Finkel
Attorney, Agent, or Firm—Richard E. Brown

[57] ABSTRACT

A catheter of a thermoplastic elastomeric hydrophilic polyurethane is coated on at least the outside surface with a hydrophobic polymer and expands to a larger lumen size in about 3 to 15 minutes when contacted with an aqueous liquid. The hydrophilic polyurethane may be synthesized by one-shot bulk polymerization, and may be melt extruded into a base tubing and dip coated with the hydrophobic polymer, or the hydrophilic polyurethane and hydrophobic polymer may be coextruded. The catheter may have multiple lumens and may include an antithrombogenic agent, antiinfective agent and radiopaque agent.

17 Claims, 4 Drawing Sheets

EXPANDABLE CATHETER HAVING HYDROPHOBIC SURFACE

BACKGROUND OF THE INVENTION

1. Field of the Invention

This invention relates to catheterization of a patient, and more particularly relates to a catheter which expands to a larger gauge size when it comes into contact with an aqueous liquid.

2. Background of the Invention

Catheterization procedures conventionally include puncture of a patient's skin and insertion of a catheter into a body cavity, such as the blood stream, using some type of catheter insertion device. For patient comfort, it is highly desirable that the catheter, and perforce any insertion equipment, be of the smallest possible cross-sectional area during insertion. It is nevertheless evident that the catheter lumen must be large enough to achieve the required rate of administration of a medicament solution through the catheter or removal of body fluids or components thereof, such as blood cells, which may be destroyed if forced through a lumen which is too small.

Catheters of the prior art have generally been made of rigid polymeric materials which do not substantially change in cross-section when contacted with a body fluid. Exemplary of such conventional catheters is the Insyte ® line of catheters available from the Deseret division of Becton, Dickinson and Company, Sandy, Utah.

Recently, hydrophilic polymers which absorb water and expand, often termed hydrogels, have been disclosed. Gould et al., in U.S. Pat. No. 4,454,309 discloses hydrophilic polyurethane diacrylate thermoset compositions which swell on insertion in water and may be molded and cured to form shaped products.

U.S. Pat. No. 4,883,699 to Aniuk et al. discloses a tubing having a nonhydrophilic polyurethane component and a hydrophilic polyvinyl alcohol component. The tubing is said to absorb water and swell while retaining tensile strength.

U.S. Pat. Nos. 4,781,703, 4,840,622 and 4,846,812 disclose catheters fabricated of a composition which includes a nonhydrophilic first component and a hydrophilic polyurethane diacrylate second component. When contacted with a liquid, the composition swells and softens due to absorption of the liquid, causing the catheter to increase in cross sectional area.

In similar fashion, U.S. Pat. No. 4,668,221 to Luther discloses a catheter made of hydrophilic polymer which fits over a stylet for insertion. The catheter, on contact with blood, swells and softens so that the stylet can be removed.

Copending application Ser. No. 499,145 of common assignee herewith, discloses a polyurethane catheter tubing having stiffening stripes of a different polymer encapsulated therein.

While the above disclosures have advanced the art of catheter design, further improvements are needed. The present invention addresses this need.

SUMMARY OF THE INVENTION

A catheter tubing comprises a thermoplastic, elastomeric, hydrophilic base polyetherurethane (HPEU) and a coating of a hydrophobic polymer laminated thereon. The HPEU has a hard segment (HS) content of 25 to 75% and is the reaction product of at least a diisocyanate, a polyglycol component containing polyethyleneoxide glycol (PEG) and a chain extender. In the present disclosure, all percentages are by weight. The preferred HPEU has at least 50% PEG and the preferred hydrophobic polymer is a polyurethane having a HS content of 50 to 90% and/or a water absorption of about 10% or less.

In other embodiments of the invention, the tubing may have multiple lumens, and may have one or more stripes of a radiopaque material encapsulated by the HPEU.

The tubing is formed by melt processing methods such as coextrusion or extrusion combined with dip coating and does not require any curing or crosslinking. When the tubing is brought into contact with an aqueous liquid, it absorbs the liquid, softens and expands whereby the lumen increases in cross-sectional area.

The HPEU of the most preferred catheter of the invention is the reaction product of high molecular weight PEG, 4,4'-diphenylmethane diisocyanate (MDI) and a low molecular weight diol chain extender, and expands by absorbing 50 to 200% of its weight of water so that the lumen increases in diameter by about 5 to 50%. The most preferred HPEU is the reaction product of MDI, PEG of about 8,000 molecular weight and 1,4-butanediol (BDO) as the extender.

In other embodiments of the catheter of the invention, the HPEU and/or the hydrophobic laminate may have an antithrombogenic agent, such as heparin, affixed to the surface and/or an antiinfective agent either affixed to the surface or distributed substantially evenly (hereinafter referred to as bulk distributed) throughout the HPEU or hydrophobic laminate.

Thus, the invention provides an expandable/swellable softening catheter having significant advantages over prior art catheters for central venous, and particularly for peripheral catheter applications. It retains the advantage of prior art expandable catheters of a smaller gauge catheter for less painful insertion and expansion to a larger gauge size after insertion. However, prior art expandable catheters, as disclosed in the aforementioned U.S. Pat. Nos. 4,781,703, 4,840,622 and 4,846,812 do not soften sufficiently rapidly to obviate the danger of vein puncture or phlebitis during advancement and positioning or expand sufficiently rapidly in cross-sectional area to administer a medicament at high level, such as blood plasma, in an emergency situation. In addition, these catheters provide a transition zone of gradually decreasing wall thickness or a reinforcing tube to overcome kinking. The transition zone of these catheters is formed by applying a conventional drawing procedure to a preformed tubing. This drawing is an additional process step which adds to the cost of manufacture. In contrast, the catheter of the invention is of constant and uniform outside diameter and overcomes kinking because of the high HS of the hydrophobic coating. It thus is manufactured by conventional extrusion equipment without any post forming steps.

Still another disadvantage of these prior art catheters is rapid withdrawal of water from the patient's skin tissue sublayers during their insertion. As is well known, skin tissue when partially dry, sticks tenaciously to foreign material (a familiar example is the difficulty in removing many wound dressings). This is a surface effect, unrelated to the expansion, which creates a significant skin drag causing patient discomfort. Further discomfort to the patient may result from stretching of the skin when the gradually increasing diameter of the transition zone of these prior art catheters passes through the skin.

Thus, the ideal catheter would remain stiff for the length of time required for insertion and placement to prevent binding, kinking or water absorption from the skin tissue, but would absorb water rapidly from the blood and quickly become soft for safety during the time required for advancement and positioning. For most skilled practitioners, this time is about ½ to 5 minutes.

Copending application Ser. No. 499,154, of common assignee herewith, discloses an expandable catheter of a particular composition as one approach to softening within this time frame. The expandable catheter of the present invention fabricated from a thermoplastic, elastomeric, melt processable HPEU meets this time frame by virtue of the hydrophobic coating.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described and illustrated. The scope of the invention will be measured by the appended claims and their equivalents.

In accordance with the present invention, there is provided an expandable softening catheter made of an HPEU coated with a hydrophobic polyurethane. When the catheter comes into contact with a body fluid, such as blood, it absorbs water, softens and expands to a larger gauge size.

Figure 1:
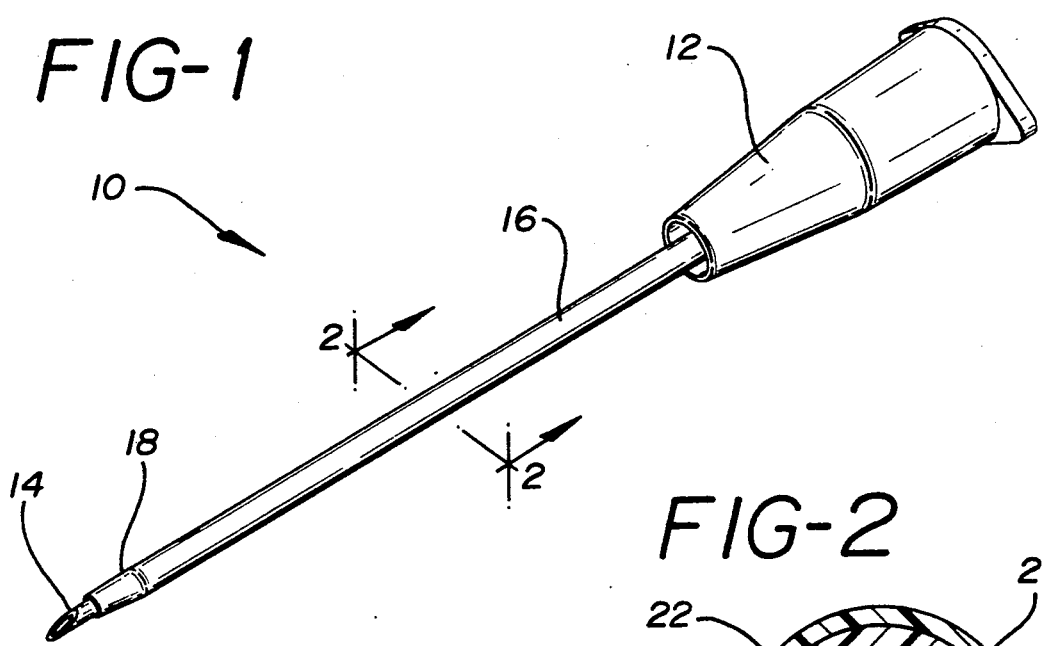
FIG. 1 is a perspective view of an intravenous catheter of the invention with associated catheter insertion device.

Adverting now to the drawings, FIG. 1 illustrates catheter tubing 10 affixed to a conventional hub 12 and catheter insertion device, shown as a hollow needle 14, for penetration of a patient's skin and placement of the catheter into the patient's blood stream. Hubs and needles are conventional in the catheter art and do not form a part of this invention. Tubing 10 includes a body portion 16 of constant and uniform outside diameter affixed at a point 18 to needle 14 by any conventional catheter tipping procedure.

Figure 2:
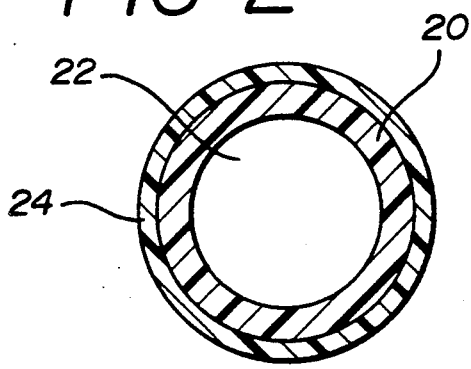
FIGS. 2-4 are sectional views of embodiments of the catheter of FIG. 1 taken along the line 2—2 thereof.
Figure 3:
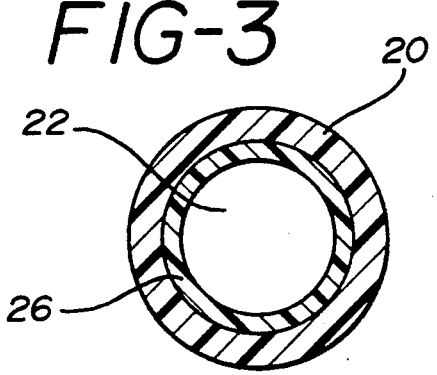
Figure 4:
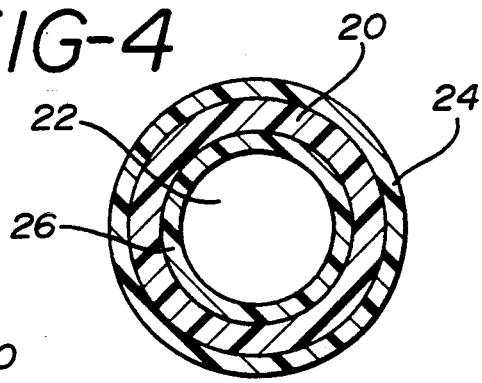

FIGS. 2-4 illustrate catheters of the invention having hydrophilic base polyurethane tubing 20 and lumen 22. In FIG. 2 and 3, hydrophobic polymer coatings 24 and 26 are on the outside wall and lumen wall of tubing 20 respectively. In FIG. 4, the hydrophobic coating is on both the outside and lumen walls.

Figure 5:
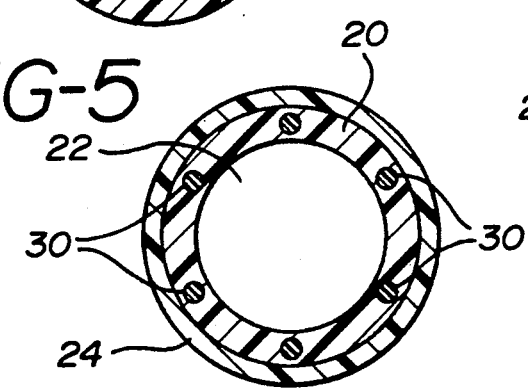
FIGS. 5-7 are sectional views of the catheters of FIGS. 2-4 respectively having stripes of a radiopaque material in the hydrophilic polymer.
Figure 6:
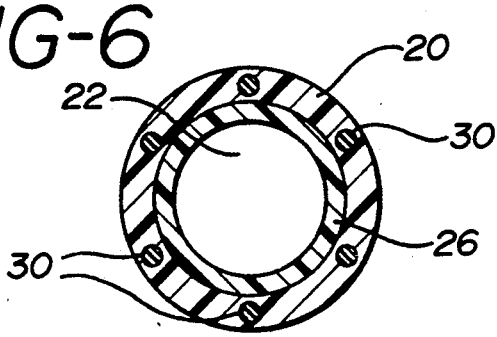
Figure 7:
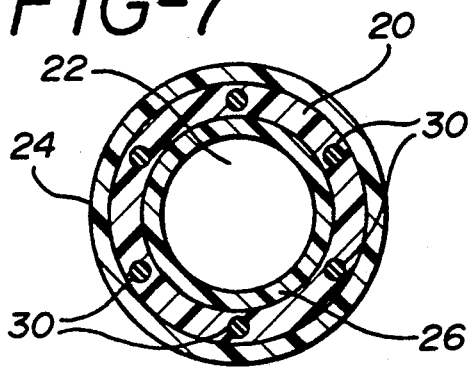
Figure 8:
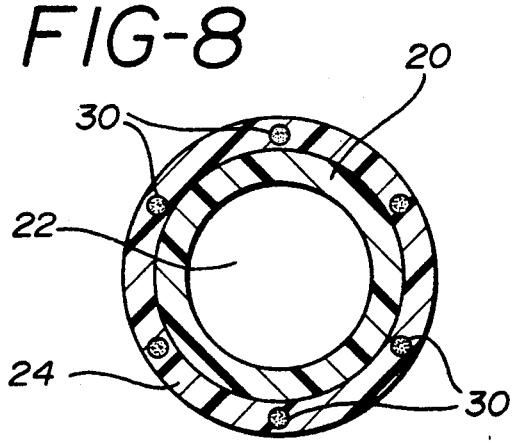
FIGS. 8 and 9 are sectional views of the catheters of FIGS. 2 and 3 respectively having stripes in the hydrophobic coating layers.
Figure 9:
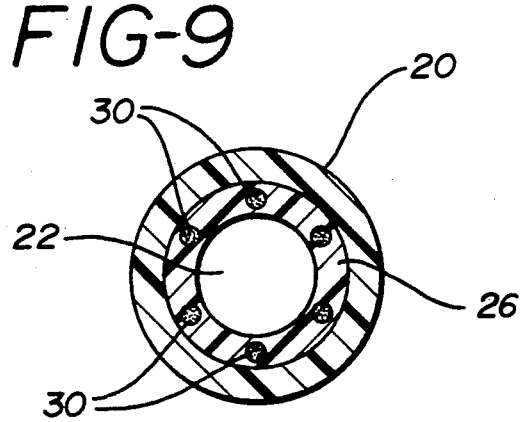

In FIGS. 5-7, the catheters of FIGS. 2-4 are shown to include stripes 30 containing a radiopaque material encapsulated by base tubing 20. FIGS. 8 and 9 show the stripes to be encapsulated by the hydrophobic coatings 24 and 26 on the outside and lumen walls of the base tubing 20.

Figure 10:
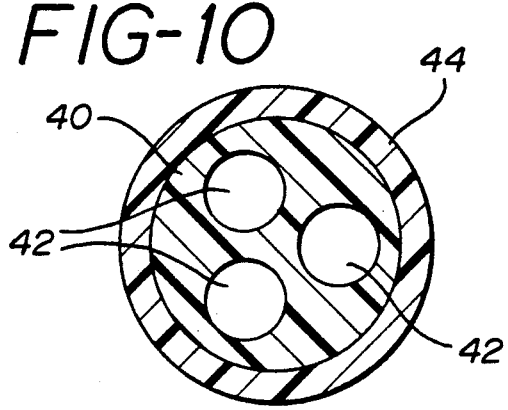
FIGS. 10-15 are sectional views of various embodiments of the catheter of FIG. 1 taken along the line 2—2 thereof having multiple lumens hydrophobic coatings on the lumen and outside walls, and radiopaque stripes in the hydrophilic polymer and the hydrophobic coating polymer.
Figure 11:
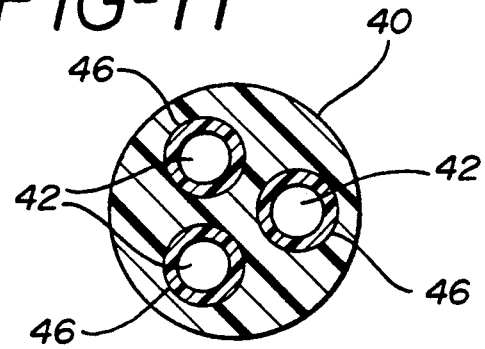
Figure 12:
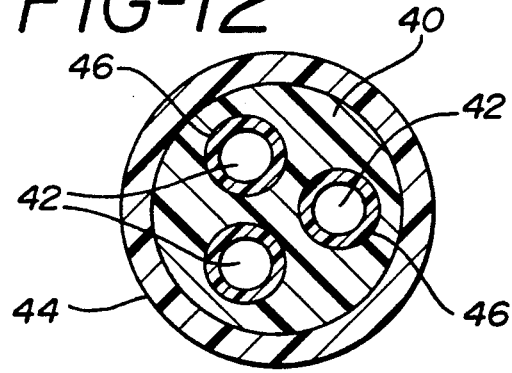

FIGS. 10-15 illustrate multiple lumen tubings of the invention. In FIGS. 10-12, catheters having hydrophilic base polyurethane tubing 40 and multiple lumens 42 are shown. The catheter of FIG. 10 has a coating 44 of hydrophobic polymer on the outside wall of the base tubing. The catheter of FIG. 11 has a hydrophobic coating 46 on the walls of the lumens. The catheter of FIG. 12 has the hydrophobic coating on both the outside and lumen walls.

Figure 13:
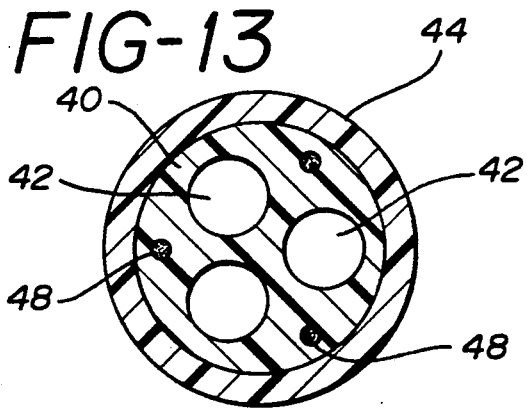
Figure 14:
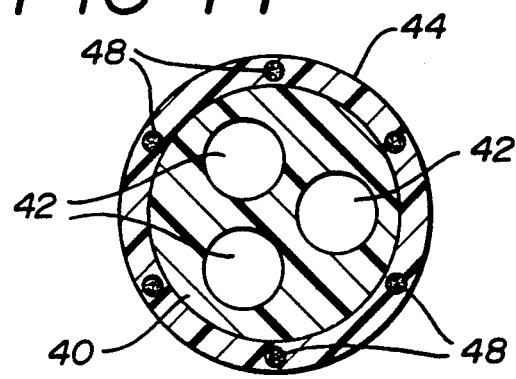
Figure 15:
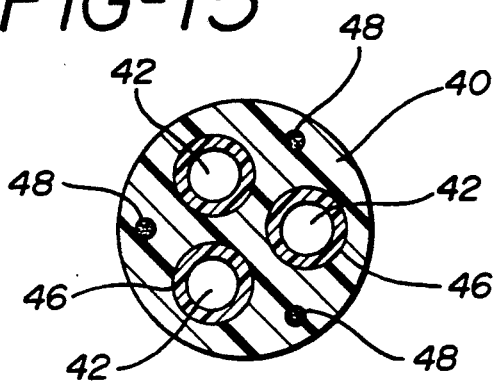

The multilumen catheter of the invention may also have stripes containing the radiopaque material. In FIG. 13, a catheter is shown having hydrophilic base tubing 40, multiple lumens 42, hydrophobic coating 44 and stripes 48 encapsulated by base polymer 40. In FIGS. 14 and 15, the stripes 48 are encapsulated by the outside hydrophobic coating 44 and lumen hydrophobic coating 46 respectively.

The HPEU includes three essential ingredients, a diisocyanate, PEG and a chain extender. Other components may be included as described below.

Suitable diisocyanates are aromatic diisocyanates such as MDI, 3,3'-diphenylmethanediisocyanate and toluene diisocyanate, alicyclic diisocyanates such as isophorone diisocyanate and 4,4'-dicyclohexylmethanediisocyanate, and aliphatic diisocyanates, as, for example, hexamethylene diisocyanate. The most preferred diisocyanate is MDI. Other diisocyanates which may be used include fluorine substituted isocyanates and silicones containing isocyanate groups.

The polyether glycol component of the HPEU may be PEG, alone or mixed with from 0 to 50% by weight of another polyglycol. Suitable polyglycols which may be mixed with the PEG include polypropyleneoxide glycol, polytetramethyleneoxide glycol (PTMEG), a fluorinated polyglycol and a silicone glycol. These glycols are substantially hydrophobic, and by mixing them with a suitable quantity of the PEG, the degree of hydrophilicity of the HPEU may be tailored according to the desired extent of expansion. A particularly useful silicone glycol is commercially available from Dow Corning Corp. under the designation 4-3667 fluid (formerly Q4-3667).

The PEG of the HPEU may have a molecular weight of about 650 to 16,000, preferably about 3,350 to 12,000. The most preferred PEG has a molecular weight of about 8,000. In accordance with the present invention, it has been found that the catheter made from an HPEU containing PEG 8000 is stiffer when it is dry, gives better mechanical properties both wet and dry and expands significantly more upon hydration than a catheter made from an HPEU based on a low molecular weight PEG.

Suitable chain extenders may be water and/or a low molecular weight branched or unbranched diol, diamine or aminoalcohol of up to 10 carbon atoms, optionally fluorinated, or mixtures thereof. Representative nonlimiting examples of chain extenders are BDO; ethylene glycol; diethylene glycol; triethylene glycol; 1,2-propanediol; 1,3-propanediol; 1,6-hexanediol; 1,4-bis-hydroxymethyl cyclohexane, hydroquinone dihydroxyethyl ether, ethanolamine, ethylenediamine and hexamethylenediamine. Preferred chain extenders are 1,6-hexanediol, ethylenediamine, hexamethylenediamine and water, most preferably, BDO.

The percentages of the components may be such that the hard segment of the HPEU may be from about 25 to 75%, preferably from about 30 to 60%, most preferably about 40 to 55% of the total weight of the formulation. From the predetermined percentage of hard segment, the proportions of the components may readily be calculated.

The HPEU of the invention has excellent wet and dry physical properties, having tensile properties in the range of 2,000 to 10,000 pounds per square inch (psi). It may absorb about 10 to 200, preferably about 50 to 150% of its weight in water wherein water absorption increases with increasing soft segment content and increasing PEG content and molecular weight. Upon absorption of water, a tubing extruded therefrom may increase from 5 to 75%, preferably about 15 to 40%, most preferably about 25% in inside diameter.

The hydrophobic coating may be of any hydrophobic polymer which can be coextruded with the HPEU or which can be dip coated onto the HPEU. Suitable polymers are, for example, silicone latex, polyvinyl chloride or a polyolefin such as polyethylene or polypropylene. The preferred hydrophobic polymer is a polyurethane which absorbs about 10% or less by weight of water. Preferred hydrophobic polyurethanes are synthesized from the diisocyanates and extenders described above for the HPEU, and may include the aforementioned polypropyleneoxide glycol, fluorinated glycol or silicone glycol in the soft segment. Most preferably, PTMEG having a molecular weight of about 650 to 16,000, preferably about 2,000, is used in the soft segment. These hydrophobic polyurethanes may have a HS of about 35 to 75, preferably about 45 to 65, most preferably about 60%.

If desired, the hydrophobic coating may be lubricated with any conventional lubricant, such as silicone to improve catheter insertion characteristics.

It will be apparent that expansion of the catheter requires that water be able to pass through the hydrophobic coating to reach the HPEU. Thus, a factor in determining a suitable thickness for the hydrophobic coating is the rate of water passage. In practice, a nonlimiting coating thickness of about 0.1 to 3.0 mils has been found to be suitable. Preferably the coating may be about 0.5 to 1.0 mil thick. Determination of the preferred thickness to obtain the desired catheter properties is easily within the purview of one skilled in the art.

Any conventional procedure for polyurethane synthesis may be used to prepare the HPEU and hydrophobic polyurethane of the invention. A two step procedure including synthesis of an isocyanate capped prepolymer followed by chain extension may be used. Preferably a one shot or bulk polymerization method is used wherein all the ingredients are combined at one time. These conventional synthesis procedures for polyurethanes are well known to those skilled in the polyurethane art.

Multilumen catheters are also well known in the art (U.S. Pat. No. 4,838,881 to Bennett and references cited therein). Such multilumen catheters are made conventionally by extrusion techniques in which the shape of the catheter is determined by the shape of a mandrel over which it is formed from a polymer melt or by the shape of a die through which the melt is forced. Also well known are coextrusion techniques in which two or more thermoplastic melts of the same or different polymers are combined prior to passage through a die of the desired shape. The catheter of the present invention may be multilumen or single lumen wherein either or both of the outside wall of the HPEU tubing and the wall of one or more lumens is coated with the hydrophobic polymer.

In another embodiment of the catheter of the invention, a conventional radiopaque material, such as barium sulfate or bismuth trioxide may be compounded with the HPEU or the hydrophobic polyurethane prior to extrusion to give a catheter having bulk distributed radiopaque. The preferred configuration for the radiopaque is a stripe coextruded with the HPEU so that the stripe is encapsulated by the HPEU. Alternatively, the die may be shaped so that the stripe of radiopaque is encapsulated by the hydrophobic coating layer. Coextrusion of radiopaque stripes is wholly conventional so that a tubing of the invention having, for example, a hydrophobic layer coated over a hydrophilic layer containing the radiopaque stripe may readily be obtained in a single coextrusion operation.

Coextrusion in accordance with the invention may be performed with any conventional and commercially available coextrusion equipment. Suitable coextrusion apparatus may be purchased, for example, from Genca Cable Company, Clearwater, Fla., or from Wayne Machine and Die Company, Totowa, N.J. This conventional apparatus may of course be used with custom dies for fabrication of any specific article of the invention. No further details for this aspect of the invention are deemed necessary for a complete understanding of this aspect of the invention by those skilled in the extrusion art.

Dip coating is an alternative procedure for laminating the hydrophobic polymer coating onto the HPEU tubing. The tubing may be dipped into a solution of the hydrophobic polymer in a suitable solvent, withdrawn from the solvent, and the solvent flashed off. Useful solvents are dimethylacetamide (DMAC), dimethylformamide, N-methylpyrrolidone, toluene, methyl ethyl ketone, petroleum ether, isopropanol and propylene glycol methyl ether acetate (PGMEA). A preferred solvent is a 1:1 by volume mixture of DMAC and PGMEA.

The catheter of the invention may have an antiinfective agent and/or an antithrombogenic agent associated therewith. Suitable antithrombogenic agents are prostaglandins, urokinase, streptokinase, tissue plasminogen activator, coumadin, dicumerol, protamine sulfate, hirudin and heparinoids. Preferred antithrombogenic agents are sulfonated heparinoids, such as dextran sulfonate, most preferably heparin or a salt thereof. Suitable nonlimiting antiinfective agents as known in the art include all chemical and biological agents which would result in an antiinfective effect when placed in the presence of bacteria, fungi, parasites or viruses. Examples of suitable agents include chlorhexidine and chlorhexidine salts, biguanides, bisbiguanides and salts thereof, chlorine and chlorine dioxide forming chemicals, other chlorine forming compounds, other halide containing agents including bromine and iodine, quaternary ammonium or other surfactant moieties, oxidizing agents, phenolic agents, chlorinated phenols, heavy metals and antibiotic-zeolite agents, antifungal agents, antiparasite agents, antiviral agents and antibiotics. Specific examples include chlorhexidine, alexidine and salts thereof such as dihydrochloride, dihydroiodide, diperchlorate, dinitrate, dinitrite, sulphate, sulphite, thiosulphate, diacid phosphate, difluorophosphate, diformate, diacetate, dipropionate, di-isobutyrate, di-n-valerate, dicaproate, malonate, succinate, malate, tartrate, dimonoglycolate, monodiglycolate, dilactate, di-α-hydroxyisobutyrate, digluconate, diglucoheptonate, di-isophthalate, di-2-hydroxynapthoate, and embonate; polyhexamethylen biguanide hydrochloride; calcium hypochlorite, sodium hypochlorite, chloramine, chloramine T; povidoneiodine formulations, 5,4'-dibromosalicylanilide, 3,5,4'-tribromosalicylanilide, parachlorometaxylenol, alkylparabens such as methyl- and ethylparaben, hexachlorophene, tetrachlorophene; triphenyl bismuthine, triclosan, phenol, nitrophenyl acetate, phenyl hydrazine; benzalkonium chloride, cetylpyridinium chloride, pseudoureas, metasulfobenzoate of dexamethasone; silver, and copper containing compounds and zeolites such as silver sulfadiazine, tetracycline and tetracycline type antibiotics, penicillin and penicillin-type antibiotics, cephalosporin and cephalosporin-type antibiotics, polyene and polypeptide-type antibiotics, 5 and 8 aminoquinoline-type antibiotics, streptomycin and streptomycin-type antibiotics, macrolide antibiotics and DNA inhibiting antibiotics such as actinomycin and kanamycin.

The antithrombogenic agent may be coated onto the surface of the expandable catheter by conventional methods. For example, it may be covalently bonded to the surface, or a complex of heparin with a quaternary salt may be used. Such complexes and their application to polymeric surfaces are well known in the art, (Hu et al., U.S. Pat. No. 4,865,870, McGary et al. in U.S. Pat. No. 4,678,660). If the antiinfective agent contains a carboxyl group, it may also be complexed with the quaternary salt and coated by the above methods.

Preferably, the antiinfective agent and the hydrophobic polymer may be blended in particulate form by any suitable mixing technique, such as stirring or tumbling the polymer pellets and antiinfective agent together, or preferably by conventional twin screw extruding. In the latter process, the ingredients may be simultaneously uniformly blended, melted and coextruded with the HPEU into catheter tubing using a commercial twin screw extruder such as the Werner and Pfleiderer Model ZDSK-28 unit. By this method, the catheter of the invention has the antiinfective agent bulk distributed uniformly throughout the hydrophobic coating.

Figure 16:
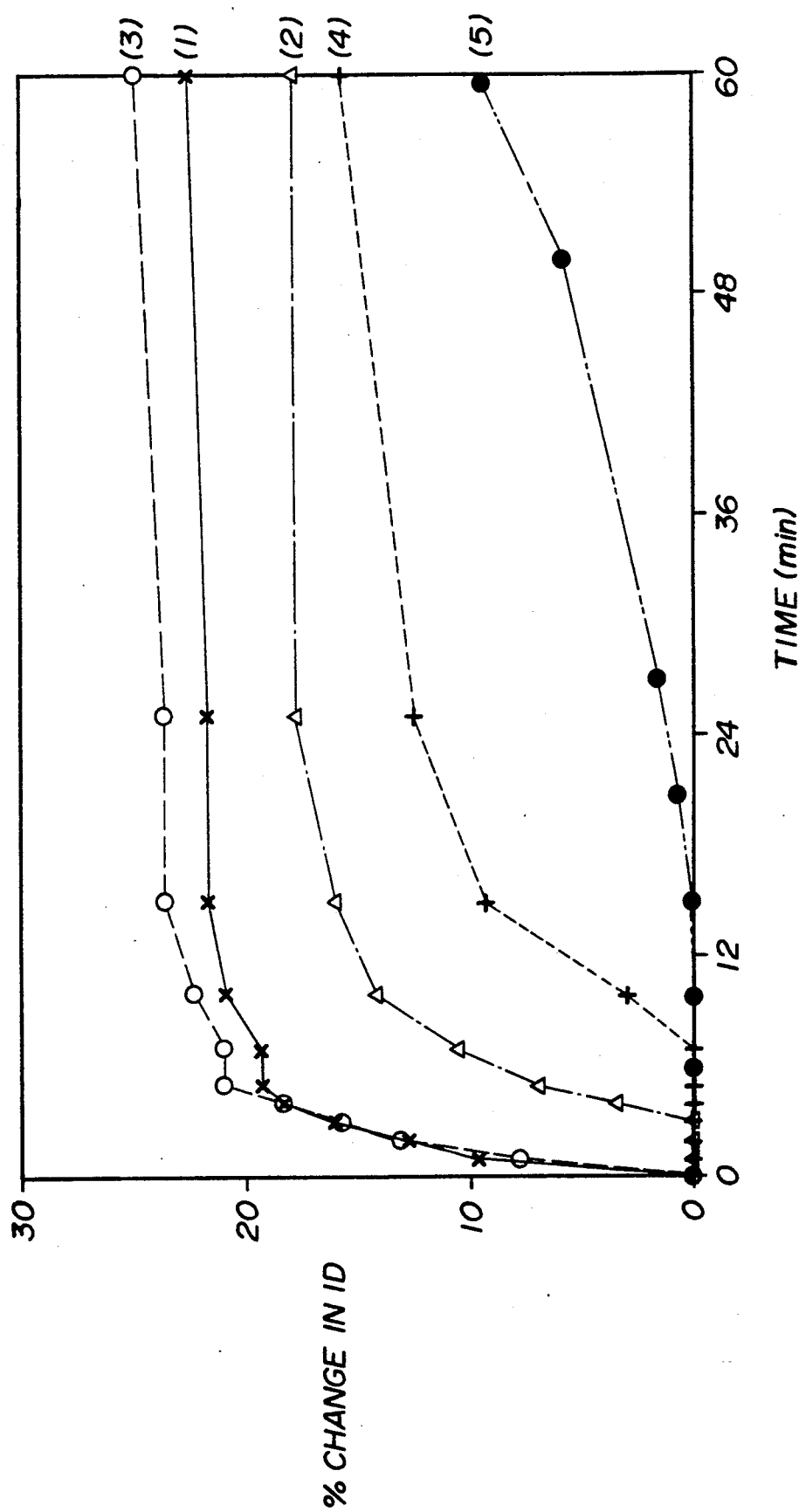
FIG. 16 compares the change in the inside diameter (ID) over time of the coated catheter of the invention with uncoated expandable catheters.

The swell rate of the coated expandable catheter of the invention was compared with a noncoated control and with the noncoated hydrophilic expandable catheter of the aforementioned U.S. Pat. No. 4,781,703. This experiment is described in Example III and the data of Table I is illustrated graphically in FIG. 16.

It is seen from the swell rate data that the uncoated controls begin absorbing water almost instantly on contact with water and have expanded up to 10%, i.e., about one half of their total expansion, in 1 minute and are substantially fully expanded in 5 minutes. The hydrophobic coating of the invention prevents any substantial expansion for about 3 minutes and expansion is substantially complete in about 10 minutes. On the other hand, the expandable catheter of U S. Pat. No. 4,781,703 does not show any substantial expansion for 30 minutes.

The following Examples are provided to further describe the invention but are not to be considered as limitative of the invention.

EXAMPLE I

A. Hydrophilic Polyurethane Synthesis

Materials

PEG (Carbowax®) of various molecular weights (600, 1,450, 3,350, 8,000) was obtained from Union Carbide Corp. and used as received. Determination of the hydroxyl number by the phthalic anhydride-pyridine method and the water content by Karl Fisher titration were performed to verify and adjust formulation stoichiometry. 1,4-Butanediol (BDO) was used as chain extender, as received, from DuPont. MDI was received from Mobay.

Synthesis

Polyurethanes were synthesized using a one shot bulk polymerization. Stoichiometric amounts of PEG and BDO were placed in the polymerization vessel and degassed at 60° C. for 30 minutes, the ratio being calculated according to the desired hard segment content. The stoichiometric amount of MDI (1.02 Index) was added and stirred vigorously until the polymerization temperature reached about 85° C. The polymer was discharged and postcured at 125° C. for 30 minutes. HPEU formulations of hard segment 35,45,50,55,60 and 65% were synthesized from each PEG.

B. Hydrophobic Polyurethane Synthesis

In the same way as described in A, hydrophobic polyurethanes were synthesized from PTMEG of various molecular weights (Polymeg®, Quaker Oats Co., Terathane®, DuPont).

EXAMPLE II

Coextrusion

A melt stream of an HPEU from a main extruder and a melt stream of a hydrophobic polymer from a coextruder are maintained separately until combined in the forward, down stream portion of an extruder head. The combined streams are passed through and emerge from a tube die (coaxial or cross head) as an integral tubing member having the hydrophobic polymer laminated over the HPEU.

EXAMPLE III

Determination of Swell Rate

Coated catheters of the invention, noncoated control catheters and a prior art catheter were dipped in water at 25° C., withdrawn from the water at a predetermined time, and the inside diameter measured and compared with the inside diameters of the dry catheters. The results of this experiment are given in Table I and illustrated in FIG. 16 wherein catheters 1–5 of Table I are identified in FIG. 16 by the numerals adjacent the graphs.

TABLE I

SWELL RATES OF COATED VS. NONCOATED 50% HARD SEGMENT PEG 8000 SWELLABLE TUBINGS

| TIME IMMERSED IN WATER | CATHETER (1) I.D. INCHES | CATHETER (1) % CHANGE | CATHETER (2) I.D. INCHES | CATHETER (2) % CHANGE | CATHETER (3) I.D. INCHES | CATHETER (3) % CHANGE | CATHETER (4) I.D. INCHES | CATHETER (4) % CHANGE | CATHETER (5) I.D. INCHES | CATHETER (5) % CHANGE |
|---|---|---|---|---|---|---|---|---|---|---|
| 0 MIN | 0.031 | — | 0.028 | — | 0.038 | — | 0.032 | — | .029 | — |
| 1 MIN | 0.034 | 9.7 | 0.028 | — | 0.041 | 7.9 | 0.032 | — | — | — |
| 2 MIN | 0.035 | 12.9 | 0.028 | — | 0.043 | 13.2 | 0.032 | — | — | — |
| 3 MIN | 0.036 | 16.1 | 0.028 | — | 0.044 | 15.8 | 0.032 | — | — | — |
| 4 MIN | 0.037− | 18.5 | 0.029 | 3.6 | 0.045 | 18.4 | 0.032 | — | — | — |
| 5 MIN | 0.037 | 19.4 | 0.030 | 7.1 | 0.046 | 21.1 | 0.032 | — | — | — |
| 7 MIN | 0.037 | 19.4 | 0.031 | 10.7 | 0.046 | 21.1 | 0.032 | — | — | — |
| 10 MIN | 0.037+ | 21.0 | 0.032 | 14.3 | 0.046+ | 22.4 | 0.033 | 3.1 | — | — |
| 15 MIN | 0.038− | 21.8 | 0.032+ | 16.1 | 0.047 | 23.7 | 0.035 | 9.4 | — | — |
| 25 MIN | 0.038− | 21.8 | 0.033 | 17.9 | 0.047 | 23.7 | 0.036 | 12.5 | .030 | 3.4 |
| 60 MIN | 0.038 | 22.6 | 0.033 | 17.9 | 0.047+ | 25.0 | 0.037 | 15.6 | .032 | 8.7 |
| 3 HRS | 0.038 | 22.6 | 0.033 | 17.9 | 0.048 | 26.3 | 0.038 | 18.8 | .036 | 22.6 |
| 6 HRS | 0.038 | 22.6 | 0.033+ | 19.6 | 0.048 | 26.3 | 0.039 | 21.9 | .037 | 26.0 |

(1) Noncoated HPEU control; 50% hard segment PEG 8000; 20 gauge
(2) Catheter (1) dip coated inside and outside with 61% hard segment hydrophobic (PTMEG) polyurethane
(3) Noncoated HPEU control; 50% hard segment PEG 8000; 18 gauge
(4) Cathter (3) dip coated inside and outside with 61% hard segment hydrophobic (PTMEG) polyurethane
(5) Noncoated prior art hydrophilic expandable catheter. (20 gauge Streamline ®, Menlo Care Inc., Palo Alto, California)

EXAMPLE IV

Catheter Placement

As a means of testing ease of catheter placement in vivo, a qualitative rabbit model was developed. The following catheters were tested:
A) Extruded 20 gauge HPEU, 45% HS
B) Extruded 20 gauge HPEU, 50% HS
C) Extruded 20 gauge HPEU, 55% HS
D) Extruded 20 gauge hydrophobic polyurethane, PTMEG, 61% HS
E) Extruded 20 gauge HPEU, 45% HS, outside solution coated (1 mil thick, from tetrahydrofuran) with hydrophobic polyurethane, PTMEG, 61% HS
F) Extruded 20 gauge HPEU, 55% HS, outside solution coated with 1 mil thick hydrophobic polyurethane, 61% HS Catheters A-F were assembled into catheter adapters, tipped by a heated die operation, lubricated with silicone and placed on production needle assemblies by standard methods. The catheters were given blind to a technician skilled in the art of catheter placement for insertion in the saphenous vein in the hind leg quarter of New Zealand white rabbits. Observations were made on initial penetration, drag on insertion and drag on removal. The results are summarized in Table II and illustrated in FIGS. 17-19.

TABLE II

| Sample | Initial Penetration | Insertion Drag | Removal Drag |
|---|---|---|---|
| A | Severe accordion effect | High | High |
| B | Moderate accordion effect | High | High |
| C | Good | Moderate | Moderate |
| D | Good | Low | Low |
| E | Good | Moderate | Moderate |
| F | Good | Low | Low |

Figure 17:
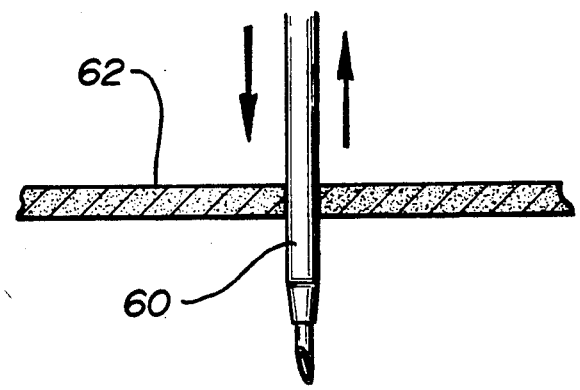
FIGS. 17-19 illustrate the effect of insertion and withdrawal of the catheter of the invention and prior art catheters through the skin of a rabbit.
Figure 18:
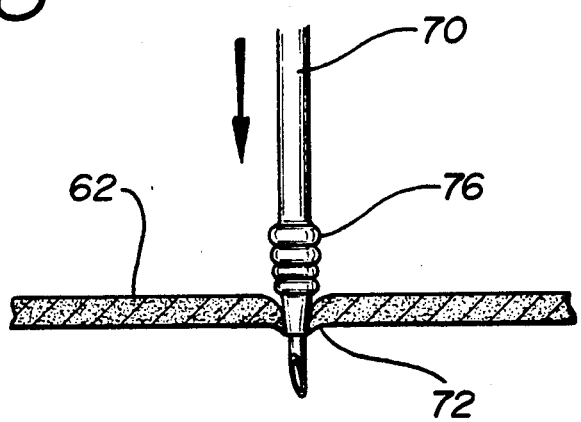
Figure 19:
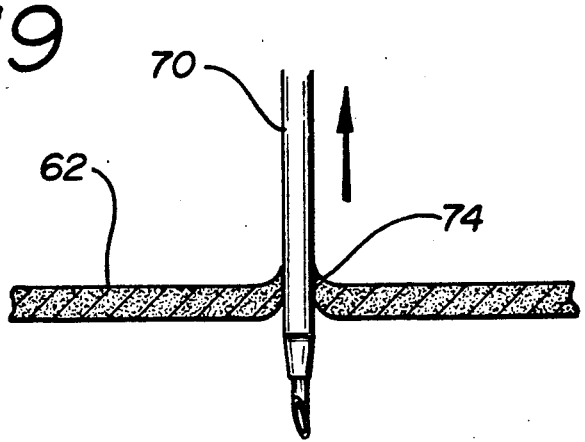

FIG. 17 shows nonexpandable control catheter 60 (sample D) of hydrophobic polyurethane to be easily inserted and removed from a rabbit's skin (direction of arrows) with no skin drag and no accordion effect. Uncoated but lubricated HPEU catheter 70 (samples A-C) is seen in FIG. 18 to cause visible skin drag 72 on insertion and in FIG. 19 to cause visible skin drag 74 on removal. This effect is due to the rapid withdrawal of water by the surfaces of these uncoated HPEU catheters from the skin sublayers causing the epidermis and tubing to stick together. In addition, uncoated HPEU catheters of low hard segment content (A and B) are so soft that the skin drag on insertion (72) causes the soft catheter to bunch up (76) in an accordion effect. In contrast, coated expandable catheter E of the invention shows good penetration without bunching equivalent to hydrophobic sample D and shows only moderate skin drag. The preferred expandable catheter of the invention (F) of high hard segment shows penetration and drag resistance comparable to hydrophobic sample D, no accordion effect and expansion when in a patient's blood stream to a very soft tubing about two gauge sizes larger.

Thus, the catheter of the invention resists water absorption for a time sufficient for a nurse or physician to insert the catheter into a patient without discomfort due to skin drag consequent to withdrawal of water from the skin sublayers. On the other hand, the catheter of the invention begins absorbing water after about 3 minutes and is substantially fully expanded after about 15 minutes to provide the softness and flexibility for patient comfort and reduction of the potential for phlebitis often seen with conventional harder nonexpanding catheters.

What is claimed is:

1. An expandable catheter consisting essentially of a substantially hydrophilic thermoplastic elastomeric polyurethane tubing, said polyurethane comprising the reaction product of a diisocyanate, polyethyleneoxide glycol and a chain extender, and a coating of a hydrophobic polymer on a surface thereof, said tubing expanding when brought into contact with an aqueous liquid.

2. The catheter of claim 1 having multiple lumens.

3. An expandable catheter consisting essentially of:
a) a substantially hydrophilic thermoplastic elastomeric polyurethane base tubing, said polyurethane having a hard segment of 30 to 60% and consisting essentially of the reaction product of a diisocyanate, a polyglycol component comprising about 50 to 100% polyethyleneoxide glycol and 0-50% of another polyglycol and a chain extender;

b) a coating of a hydrophobic polyurethane on a surface of said tubing; and c) a stripe containing a radiopaque material in at least one of said base tubing and coating, said catheter, when brought into contact with an aqueous liquid, absorbing about 50 to 150% of its weight of said liquid and expanding whereby its inside diameter increases about 15 to 40%.

4. The catheter of claim 3 wherein said diisocyanate is selected from the group consisting of 4,4'-diphenylmethane diisocyanate, 3,3'-diphenylmethane diisocyanate, isophorone diisocyanate and hexamethylene diisocyanate.

5. The catheter of claim 3 wherein said chain extender is selected from the group consisting of 1-4-butanediol, ethylene glycol, diethylene glycol, triethylene glycol, 1,2-propanediol, 1,3-propanediol, 1,6-hexanediol, 1,4-bis-hydroxymethyl cyclohexane, hydroquinone dihydroxyethyl ether, ethanolamine, ethylenediamine and hexamethylenediamine.

6. The catheter of claim 3 wherein said polyethyleneoxide glycol has a molecular weight of about 650 to 16,000.

7. The catheter of claim 3 wherein said radiopaque agent is an inorganic radiopaque.

8. The catheter of claim 3 wherein aid hydrophobic polyurethane has a hard segment content of at least 50% and a water absorption of no more than 10%.

9. The catheter of claim 3 having multiple lumens.

10. An expandable catheter consisting essentially of:

a) a substantially hydrophilic thermoplastic elastomeric base polyurethane tubing having a hard segment of 40 to 55% and comprising the reaction product of 4,4'-diphenylmethane diisocyanate, 1-4-butanediol, and polyethyleneoxide having a molecular weight of 6,000 to 12,000;

b) a coating of a hydrophobic polyurethane on a surface of said base tubing, said hydrophobic polyurethane comprising the reaction product of 4,4'-diphenylmethane diisocyanate, butanediol and polytetramethylene ether glycol;

c) a stripe containing a radiopaque material encapsulated by one of said base tubing and said coating; said catheter, when brought into contact with an aqueous liquid, absorbing said liquid and expanding whereby its inside diameter increases about 25%; and d) an agent selected from the group consisting of an antiinfective agent and an antithrombogenic agent associated with at least one of said base tubing and said coating.

11. The catheter of claim 10 wherein said hydrophobic polymer has a hard segment content of 50 to 90%.

12. The catheter of claim 10 wherein said hydrophobic polymer has a water absorption of no more than 10%.

13. The catheter of claim 10 having multiple lumens.

14. The catheter of claim 10 wherein said agent is bulk distributed in at least one of said base polyurethane and said hydrophobic polyurethane.

15. The catheter of claim 10 wherein said agent is coated on at least one of said base polyurethane and said hydrophobic polyurethane.

16. The catheter of claim 10 wherein said antithrombogenic agent is selected from the group consisting of a prostaglandin, urokinase, streptokinase, tissue plasminogen activator and a heparinoid.

17. The catheter of claim 10 wherein said antiinfective agent is selected from the group consisting of chlorhexidine, silver sulfadiazine and an antibiotic.

* * * * *